(12) United States Patent
Deo

(10) Patent No.: US 11,610,791 B2
(45) Date of Patent: *Mar. 21, 2023

(54) TIME-VARYING FREQUENCY POWERED HEAT SOURCE

(71) Applicant: Anand Deo, Mendota Heights, MN (US)

(72) Inventor: Anand Deo, Mendota Heights, MN (US)

(*) Notice: Subject to any disclaimer, the term of this patent is extended or adjusted under 35 U.S.C. 154(b) by 676 days.

This patent is subject to a terminal disclaimer.

(21) Appl. No.: 16/548,809

(22) Filed: Aug. 22, 2019

(65) Prior Publication Data
US 2020/0118846 A1    Apr. 16, 2020

Related U.S. Application Data

(63) Continuation of application No. 16/200,120, filed on Nov. 26, 2018, now Pat. No. 10,431,478, which is a
(Continued)

(51) Int. Cl.
*H05B 6/62* (2006.01)
*H05B 1/02* (2006.01)
(Continued)

(52) U.S. Cl.
CPC .......... *H01L 21/67103* (2013.01); *A61F 7/12* (2013.01); *H01L 21/324* (2013.01);
(Continued)

(58) Field of Classification Search
CPC ............ A61F 7/12; H01L 21/324; H01L 21/67103; H01L 21/67248; H05B 1/023; H05B 6/50

USPC .......... 219/795, 770, 772, 777, 121.36, 201, 219/690, 691, 696, 497, 492; 438/9, 660, 438/710, 18; 118/723 MP, 723 E,
(Continued)

(56) References Cited

U.S. PATENT DOCUMENTS

| | | |
|---|---|---|
| 3,780,255 A | 12/1973 | Boom |
| 4,338,575 A | 7/1982 | Hartemann |

(Continued)

FOREIGN PATENT DOCUMENTS

| | | |
|---|---|---|
| CA | 2993930 A1 | 2/2017 |
| CN | 106267534 A | 1/2017 |

(Continued)

OTHER PUBLICATIONS

U.S. Appl. No. 16/780,554, filed Feb. 3, 2020, Frequency and Phase Controlled Transducers and Sensing.
(Continued)

*Primary Examiner* — Quang T Van
(74) *Attorney, Agent, or Firm* — Schwegman Lundberg & Woessner, P.A.

(57) ABSTRACT

A semiconductor or other substrate can include one or more electrodes, located directly or indirectly on the substrate, separated from each other and coupled to the substrate. At the two or more electrodes, non-zero frequency time-varying electrical energy can be received. The time-varying electrical energy can be coupled via the two or more electrodes to trigger a displacement current to activate free carriers confined within the semiconductor substrate to generate frequency-controlled heat in the semiconductor substrate.

25 Claims, 6 Drawing Sheets

Related U.S. Application Data continuation of application No. PCT/US2016/069490, filed on Dec. 30, 2016, which is a continuation of application No. 15/165,096, filed on May 26, 2016, now Pat. No. 9,536,758.

(51) Int. Cl.

| H01L 21/67 | (2006.01) |
|---|---|
| H01L 21/324 | (2006.01) |
| A61F 7/12 | (2006.01) |
| H05B 6/50 | (2006.01) |

(52) U.S. Cl.
CPC ....... *H01L 21/67248* (2013.01); *H05B 1/023* (2013.01); *H05B 6/50* (2013.01)

(58) Field of Classification Search
USPC ............... 118/723 MW, 728, 729, 715, 679; 156/345.51, 345.55
See application file for complete search history.

(56) References Cited

U.S. PATENT DOCUMENTS

| | | | |
|---|---|---|---|
| 4,945,912 | A | 8/1990 | Langberg |
| 5,037,395 | A | 8/1991 | Spencer |
| 5,057,105 | A | 10/1991 | Malone et al. |
| 5,191,883 | A | 3/1993 | Lennox et al. |
| 5,257,635 | A | 11/1993 | Langberg |
| 5,260,020 | A | 11/1993 | Wilk et al. |
| 5,290,490 | A | 3/1994 | Nied et al. |
| 5,498,261 | A | 3/1996 | Strul |
| 5,891,182 | A | 4/1999 | Fleming |
| 6,157,804 | A | 12/2000 | Richmond et al. |
| 6,387,052 | B1 | 5/2002 | Quinn et al. |
| 6,426,277 | B1 * | 7/2002 | Bae ................. H01L 21/324 438/522 |
| 6,443,547 | B1 | 9/2002 | Takahashi et al. |
| 6,511,851 | B1 | 1/2003 | Payne et al. |
| 6,537,864 | B1 | 3/2003 | Aya et al. |
| 6,537,927 | B1 | 3/2003 | Son |
| 6,825,734 | B2 | 11/2004 | Clark |
| 6,901,683 | B2 | 6/2005 | Lyle et al. |
| 7,133,180 | B2 | 11/2006 | Ilchenko et al. |
| 7,160,297 | B2 | 1/2007 | Nesbitt |
| 7,274,262 | B2 | 9/2007 | Ham et al. |
| 7,317,216 | B2 | 1/2008 | Holm-kennedy |
| 7,393,501 | B2 | 7/2008 | Zumeris et al. |
| 7,429,719 | B1 | 9/2008 | Spetz |
| 7,586,381 | B2 | 9/2009 | Rohde et al. |
| 7,844,345 | B2 | 11/2010 | Boling et al. |
| 8,698,570 | B2 | 4/2014 | Afshari et al. |
| 8,933,416 | B2 | 1/2015 | Arcand et al. |
| 9,008,793 | B1 | 4/2015 | Cosman, Sr. et al. |
| 9,362,604 | B2 | 6/2016 | Denis et al. |
| 9,536,758 | B1 | 1/2017 | Deo |
| 10,431,478 | B2 | 10/2019 | Deo |
| 10,515,831 | B2 | 12/2019 | Deo |
| 10,553,462 | B2 | 2/2020 | Deo |
| 11,152,232 | B2 | 10/2021 | Deo |
| 2002/0065052 | A1 | 5/2002 | Pande et al. |
| 2002/0120296 | A1 | 8/2002 | Mech et al. |
| 2003/0164371 | A1 | 9/2003 | Bergstrom et al. |
| 2003/0205571 | A1 | 11/2003 | Flugstad et al. |
| 2005/0068116 | A1 | 3/2005 | Ham et al. |
| 2005/0083785 | A1 | 4/2005 | Shiokawa et al. |
| 2006/0071237 | A1 | 4/2006 | Deboy et al. |
| 2007/0161263 | A1 | 7/2007 | Meisner |
| 2007/0260239 | A1 | 11/2007 | Podhajsky et al. |
| 2009/0054881 | A1 | 2/2009 | Krespi |
| 2009/0071952 | A1 | 3/2009 | Kuwabara |
| 2009/0131845 | A1 | 5/2009 | Gurtner et al. |
| 2009/0131854 | A1 | 5/2009 | DiCarlo et al. |
| 2009/0162954 | A1 | 6/2009 | Griffin, Jr. et al. |
| 2009/0256649 | A1 | 10/2009 | Taniguchi |
| 2010/0003021 | A1 | 2/2010 | Paulus |
| 2010/0036375 | A1 | 2/2010 | Regadas |
| 2010/0036405 | A1 | 2/2010 | Giordano et al. |
| 2010/0191232 | A1 | 7/2010 | Boveda |
| 2010/0217259 | A1 | 8/2010 | Strauss |
| 2010/0249692 | A1 | 9/2010 | Dacey, Jr. et al. |
| 2010/0286691 | A1 | 11/2010 | Kerr et al. |
| 2011/0137390 | A1 | 6/2011 | Hill |
| 2011/0152790 | A1 | 6/2011 | Dacey, Jr. et al. |
| 2011/0226759 | A1 | 9/2011 | Wander et al. |
| 2012/0029500 | A1 | 2/2012 | Jenson |
| 2012/0152935 | A1 | 6/2012 | Kitaizumi et al. |
| 2012/0261405 | A1 | 10/2012 | Kurose et al. |
| 2012/0330393 | A1 | 12/2012 | Janik et al. |
| 2013/0096595 | A1 | 4/2013 | Myhr et al. |
| 2013/0282201 | A1 | 10/2013 | Mathur et al. |
| 2014/0088674 | A1 | 3/2014 | Bradley |
| 2014/0257272 | A1 | 9/2014 | Clark, III et al. |
| 2015/0119877 | A1 | 4/2015 | Jameson et al. |
| 2015/0289316 | A1 | 10/2015 | Shimizu et al. |
| 2017/0258628 | A1 | 9/2017 | Awasthi |
| 2018/0042667 | A1 | 2/2018 | Pappone et al. |
| 2018/0323090 | A1 | 11/2018 | Deo |
| 2019/0109024 | A1 | 4/2019 | Deo |
| 2020/0013644 | A1 | 1/2020 | Deo |
| 2020/0135507 | A1 | 4/2020 | Deo |
| 2020/0176283 | A1 | 6/2020 | Deo |
| 2022/0108899 | A1 | 4/2022 | Deo |

FOREIGN PATENT DOCUMENTS

| | | |
|---|---|---|
| EP | 3113281 A1 | 1/2017 |
| GB | 1529941 A | 10/1978 |
| WO | WO-2012153529 A1 | 11/2012 |
| WO | WO-2016181397 A1 | 11/2016 |
| WO | WO-2017204860 A1 | 11/2017 |
| WO | WO-2019010238 A1 | 1/2019 |
| WO | 2020010247 | 1/2020 |

OTHER PUBLICATIONS

"U.S. Appl. No. 16/666,773, Preliminary Amendment filed Jan. 21, 2020", 7 pgs.

"U.S. Appl. No. 16/780,554, Non Final Office Action dated Sep. 22, 2020", 9 pgs.

"U.S. Appl. No. 16/780,554, Response filed Dec. 15, 2020 to Non Final Office Action dated Sep. 22, 2020", 11 pgs.

"International Application Serial No. PCT/US2019/040588, International Preliminary Report on Patentability dated Jan. 14, 2021", 7 pgs.

"U.S. Appl. No. 15/165,096, Notice of Allowance dated Aug. 31, 2016", 9 pgs.

"U.S. Appl. No. 16/027,139, Examiner Interview Summary dated Jun. 21, 2019", 3 pgs.

"U.S. Appl. No. 16/027,139, Non Final Office Action dated Mar. 22, 2019", 13 pgs.

"U.S. Appl. No. 16/027,139, Non Final Office Action dated Nov. 19, 2018", 11 pgs.

"U.S. Appl. No. 16/027,139, Notice of Allowance dated Jul. 29, 2019", 8 pgs.

"U.S. Appl. No. 16/027,139, Response filed Dec. 10, 2018 to Non Final Office Action dated Nov. 19, 2018", 12 pgs.

"U.S. Appl. No. 16/027,139, Response filed Jun. 20, 2019 to Non-Final Office Action dated Mar. 22, 2019", 16 pgs.

"U.S. Appl. No. 16/200,120, Corrected Notice of Allowability dated Aug. 26, 2019", 2 pgs.

"U.S. Appl. No. 16/200,120, Examiner Interview Summary dated Apr. 11, 2019", 3 pgs.

"U.S. Appl. No. 16/200,120, Notice of Allowance dated May 22, 2019", 5 pgs.

"U.S. Appl. No. 16/200,120, Response filed Mar. 25, 2019 to Non-Final Office Action dated Jan. 24, 2019", 16 pgs.

"U.S. Appl. No. 16/200,120, Supplemental Response filed Apr. 8, 2019 to Non-Final Office Action dated Jan. 24, 2019", 10 pgs.

(56) References Cited

OTHER PUBLICATIONS

"U.S. Appl. No. 16/502,989, Preliminary Amendment filed Jul. 11, 2019", 4 pgs.
"European Application Serial No. 16903365.1, Extended European Search Report dated May 17, 2019", 8 pgs.
"International Application Serial No. PCT/US2016/069490, International Preliminary Report on Patentability dated Jul. 10, 2018", 1 pg.
"International Application Serial No. PCT/US2016/069490, International Search Report dated Mar. 8, 2017", 2 pgs.
"International Application Serial No. PCT/US2016/069490, Written Opinion dated Mar. 8, 2017", 7 pgs.
"International Application Serial No. PCT/US2018/040812, international Search Report dated Sep. 19, 2018", 2 pgs.
"International Application Serial No. PCT/US2018/040812, Written Opinion dated Sep. 19, 2018", 6 pgs.
Beringer, Robert, "The Measurement of Wavelength—Chapter 5 from Technique of Microwave Measurements", vol. 11 of MIT Radiation Laboratory Series. McGraw-Hill, New York, (1947), 58 pgs.
Gopinath, A., et al., "Capacitance Parameters of Discontinuities in Microstriplines", IEEE Trans. On Microwave Theory and Techniques, vol. MTT-26, No. 10, (Oct. 1978), 831-836.
Mahan, Gerald, et al., "Thermoelectric Materials: New Approaches to an Old Problem", Physics Today, (Mar. 1997), 42-47.
Otoole, Ann, et al., "Thermal mitigation of Pseudomonas aeruginosa biofilms", Biofouling. Sep. 2015; 31(8): 665-675., (2015), 20 pgs.
Richardson, Ian P., et al., "Hemodialysis Catheter Heat Transfer for Biofilm Prevention and Treatment", ASAIO J. 2016; 62(1): 92-99. doi:10.1097/MAT.0000000000000300, (2016), 17 pgs.
"U.S. Appl. No. 16/027,139, Corrected Notice of Allowability dated Sep. 20, 2019", 3 pgs.
"U.S. Appl. No. 16/027,139, Corrected Notice of Allowability dated Oct. 29, 2019", 3 pgs.
"U.S. Appl. No. 16/502,989, Corrected Notice of Allowability dated Oct. 31, 2019", 2 pgs.
"U.S. Appl. No. 16/502,989, Notice of Allowance dated Sep. 25, 2019", 9 pgs.
"International Application Serial No. PCT/US2019/040588, International Search Report dated Oct. 8, 2019", 2 pgs.
"International Application Serial No. PCT/US2019/040588, Written Opinion dated Oct. 8, 2019", 5 pgs.
"U.S. Appl. No. 16/666,773, Non Final Office Action dated Feb. 16, 2022", 13 pgs.
"U.S. Appl. No. 16/666,773, Response filed May 16, 2022 to Non Final Office Action dated Feb. 16, 2022", 8 pgs.
"U.S. Appl. No. 16/780,554, Corrected Notice of Allowability dated Sep. 15, 2021", 2 pgs.
"U.S. Appl. No. 16/780,554, Final Office Action dated Jan. 27, 2021", 7 pgs.
"U.S. Appl. No. 16/780,554, Notice of Allowance dated Apr. 29, 2021", 5 pgs.
"U.S. Appl. No. 16/780,554, Response filed Apr. 13, 2021 to Final Office Action dated Jan. 27, 2021", 10 pgs.
"European Application Serial No. 16903365.1, Communication Pursuant to Article 94(3) EPC dated May 11, 2021", 5 pgs.
"European Application Serial No. 19830071.7, Extended European Search Report dated Aug. 16, 2021", 8 pgs.
"U.S. Appl. No. 16/666,773, Final Office Action dated Jun. 16, 2022", 13 pgs.
"U.S. Appl. No. 16/666,773, Response filed Aug. 16, 2022 to Final Office Action dated Jun. 16, 2022", 9 pgs.

\* cited by examiner

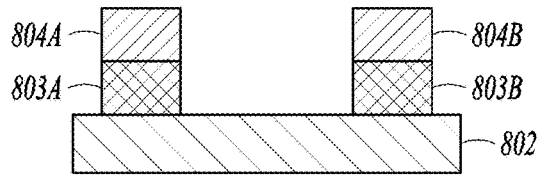 
FIG. 8A        FIG. 8B
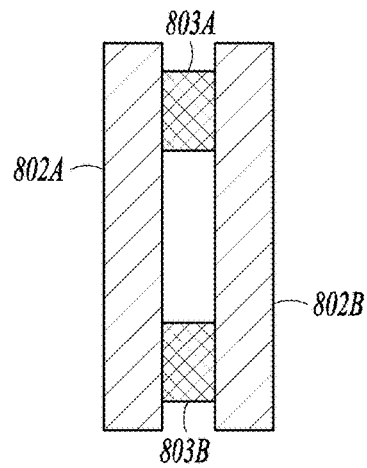 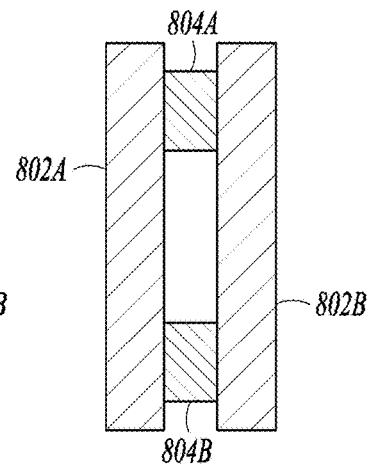 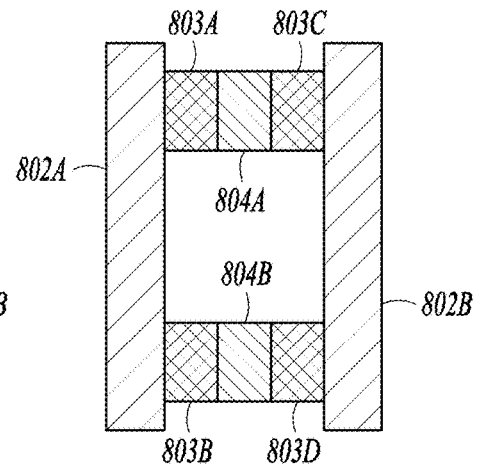
FIG. 8C        FIG. 8D        FIG. 8E
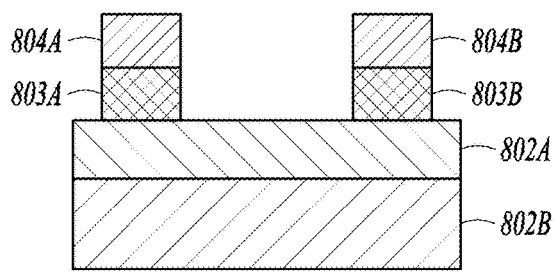
FIG. 8F

TIME-VARYING FREQUENCY POWERED HEAT SOURCE

CLAIM OF PRIORITY

This application is a continuation of, and claims the benefit of priority of Ser. No. 16/200,120, to Anand Deo, which was filed on Nov. 26, 2018, which is a continuation of, and claims the benefit of priority of PCT Patent Application No. PCT/US2016/069490, to Anand Deo, which was filed Dec. 30, 2016, which is a continuation of, and claims the benefit of priority of U.S. patent application Ser. No. 15/165,096, to Anand Deo, which was filed May 26, 2016, and which was entitled TIME-VARYING FREQUENCY POWERED SEMICONDUCTOR SUBSTRATE HEAT SOURCE, the benefit of priority of each of which is hereby claimed, and each of which is hereby incorporated by reference herein in its entirety

TECHNICAL FIELD

This document relates generally to systems and methods for establishing or adjusting temperature of a semiconductor, thin film metal, or other substrate, such as can include establishing or adjusting non-random temperature gradients in time and space in the substrate and particularly, but not by way of limitation, to substrate heating using a time-varying electric field frequency, such as for establishing a non-Brownian or non-random temperature gradient.

BACKGROUND

Many applications involve heating. Efficiency, precise control, convenience, size, and usability can be concerns with existing techniques for establishing or adjusting temperature of a target object or space.

Spetz U.S. Pat. No. 7,429,719 provides a self-regulating heater using a semiconductor as a heating element that has a fast response and is temperature limited. A biasing network operates the semiconductor to cause the semiconductor to conduct more current at lower temperatures and less current at higher temperatures. Spetz uses a field-effect transistor (FET) as a heat source and then drains the resulting current out the FET in a loop around the semiconductor in order to complete the circuit for the pass-through current.

Wander U.S. Patent Publication No. 20110226759 discusses an example of applying microwaves to a semiconductor wafer to heat the semiconductor wafer. Wander uses a microwave cavity as the energy source, and merely places the semiconductor in the cavity as a bulk target to be heated, without providing any ability to localize heat production or gradients at one or more particular locations within the semiconductor substrate.

SUMMARY

The present inventor has recognized a need for improved techniques for establishing or adjusting temperature of, or temperature gradient in, a semiconductor, thin-film metal, or other substrate (or, indirectly, that of another object or space that is thermally coupled to the semiconductor substrate). In this document, the term "substrate" includes the layer of material that is actively excited through a non-zero frequency time-varying electric field, and can include a semiconductor substrate, a thin-film or other substrate, a quartz substrate, a diamond substrate, or other suitable substrate material or composite material. In an illustrative but non-limiting example, the non-zero frequency time-varying electric field can be capacitively coupled to a semiconductor substrate, but such coupling and such a substrate are not requirements for certain aspects of the present subject matter.

This document describes, among other things, techniques for providing controlled time-varying excitation of a semiconductor material, such for producing thermal energy in the semiconductor material. A non-zero frequency time-varying electric field can be capacitively applied (in an illustrative, non-limiting example), such as via local electrodes, to the semiconductor material. The frequency can be adjusted, such as to a desired degree of excitation, such as to induce majority carriers in the semiconductor to oscillate to generate heat. Other techniques for introducing energy into the semiconductor may be used in combination with such a technique. Such localized heat production in time and space can permit control or management of one or more temperature gradients in the semiconductor substrate.

A non-limiting overview of certain aspects of the present subject matter follows immediately below.

Aspect 1 can include or use subject matter (such as an apparatus, a system, a device, a method, a means for performing acts, or a device readable medium including instructions that, when performed by the device, can cause the device to perform acts), such as can include or use a semiconductor substrate. A temperature sensor can be located in association with the semiconductor substrate, such as to sense a temperature associated with the semiconductor substrate. Two or more electrodes can be located directly or indirectly on the semiconductor substrate. The electrodes can be separated from each other and capacitively coupled to the semiconductor substrate. The electrodes can be configured to receive a non-zero frequency time-varying electrical energy such as can be capacitively coupled by the electrodes to the semiconductor substrate such as to trigger a displacement current to generate heat in the semiconductor substrate. The heat generation can be controlled using information received from the temperature sensor to control the time-varying energy received by the electrodes.

Aspect 2 can include or use, or can optionally be combined with the subject matter of Aspect 1 to optionally include or use an electric field signal generator circuit, which can be configured to generate the time-varying electrical energy. The non-zero frequency can be at or can exceed an RF frequency or a microwave frequency such as for wired or wirelessly coupling to the electrodes. A control circuit can be configured to use temperature information from the temperature sensor such as to establish or adjust at least one of: (1) an amplitude of the time-varying electrical energy generated by the electric field signal generator; (2) a frequency of the time-varying electrical energy generated by the electric field generator; or (3) an output impedance of the electric field signal generator.

Aspect 3 can include or use, or can optionally be combined with the subject matter of one or any combination of Aspects 1 through 2 to optionally include or use the electric field signal generator circuit including an output impedance that is matched to an impedance between the two or more electrodes at the specified non-zero frequency of the time-varying electrical energy generated by the electric field signal generator circuit.

Aspect 4 can include or use, or can optionally be combined with the subject matter of one or any combination of Aspects 1 through 3 to optionally include or use an impedance matching circuit included in the electric field generator or located between the electric field signal generator and at least one of the two or more electrodes to match, at a specified frequency of the electric field signal generator, the impedance between the two or more electrodes and the output impedance of the electric field signal generator.

Aspect 5 can include or use, or can optionally be combined with the subject matter of one or any combination of Aspects 1 through 4 to optionally include or use the two or more electrodes including first and second electric field nodes that can include, at a first location on the semiconductor substrate, a spacing separating the first and second electrodes. The spacing can be specified to be less than or equal to a spacing capable of generating heat in the semiconductor substrate, without requiring net charge flow into or out of the semiconductor substrate via pass-through conduction current, in response to the time-varying electrical energy received at the first and second electrodes.

Aspect 6 can include or use, or can optionally be combined with the subject matter of one or any combination of Aspects 1 through 5 to optionally include or use the one or more electrodes including electrically conductive material that can be separated from the semiconductor substrate by a dielectric layer.

Aspect 7 can include or use, or can optionally be combined with the subject matter of one or any combination of Aspects 1 through 5 to optionally include or use the temperature of the substrate capable of being adjusted by direct heating of the semiconductor substrate such as by an electric field produced by the capacitively-coupled time-varying electrical energy, without requiring indirect heat coupling to the semiconductor substrate via the dielectric.

Aspect 8 can include or use, or can optionally be combined with the subject matter of one or any combination of Aspects 1 through 7 to optionally include or use an amplitude of the time-varying electrical energy received by the electrodes being controlled using information, such as can be received from the temperature sensor, about the temperature of the semiconductor substrate such as to establish or adjust the temperature of the semiconductor substrate.

Aspect 9 can include or use, or can optionally be combined with the subject matter of one or any combination of Aspects 1 through 8 to optionally include or use a frequency of the time-varying electrical energy received by the electrodes being controlled using information, such as can be received from the temperature sensor, about the temperature of the semiconductor substrate such as to establish or adjust the temperature of the semiconductor substrate.

Aspect 10 can include or use, or can optionally be combined with the subject matter of one or any combination of Aspects 1 through 9 to optionally include or use the two or more electrodes include a first electrode that is located directly or indirectly on a first face of the semiconductor substrate and a second electrode that is located directly or indirectly an opposing second face of the semiconductor substrate.

Aspect 11 can include or use, or can optionally be combined with the subject matter of one or any combination of Aspects 1 through 10 to optionally include or use the second electrode covering enough of the opposing second face of the semiconductor substrate to form a ground plane with respect to the first electrode.

Aspect 12 can include or use, or can optionally be combined with the subject matter of one or any combination of Aspects 1 through 11 to optionally include or use the two or more electrodes including a first electrode comprising a linear trace that can be located directly or indirectly on a first face of the semiconductor substrate and a second electrode comprising a linear trace that can be located directly or indirectly on the first face of the semiconductor substrate and that can be separated from the first electrode by a specified distance.

Aspect 13 can include or use, or can optionally be combined with the subject matter of one or any combination of Aspects 1 through 12 to optionally include or use the specified distance being fixed (e.g., parallel lines).

Aspect 14 can include or use, or can optionally be combined with the subject matter of one or any combination of Aspects 1 through 13 to optionally include or use the specified distance being variable such as to form a tapered arrangement (e.g., diverging or converging).

Aspect 15 can include or use, or can optionally be combined with the subject matter of one or any combination of Aspects 1 through 14 to optionally include or use a ground plane such as can be located on an opposing second face of the semiconductor substrate such as at a specified distance from the first and second electrodes.

Aspect 16 can include or use subject matter (such as an apparatus, a system, a device, a method, a means for performing acts, or a device readable medium including instructions that, when performed by the device, can cause the device to perform acts), or can optionally be combined with the subject matter of one or any combination of Aspects 1 through 15 to optionally include or use or provide a semiconductor substrate and two or more electrodes, such as can be located directly or indirectly on the semiconductor substrate, such as can be separated from each other and capacitively coupled to the semiconductor substrate. At the two or more electrodes, non-zero frequency time-varying electrical energy can be received. The time-varying electrical energy can be capacitively coupled, such as via the two or more electrodes, such as to trigger a displacement current to generate or trigger generation of heat in the semiconductor substrate. A temperature associated with the semiconductor substrate can be sensed, such as using a temperature sensor that can be located in association with the semiconductor substrate. Using information received from the temperature sensor, a temperature of the semiconductor substrate can be established or adjusted, such as by or including controlling the electrical energy received at the two or more electrodes.

Aspect 17 can include or use, or can optionally be combined with the subject matter of one or any combination of Aspects 1 through 16 to optionally include or use providing, such as to the two or more electrodes, time-varying electrical energy that can include a non-zero frequency that can be at or can exceed at least one of a RF frequency or a microwave frequency.

Aspect 18 can include or use, or can optionally be combined with the subject matter of one or any combination of Aspects 1 through 17 to optionally include or use wirelessly receiving, such as at the two or more electrodes, time-varying electrical energy that can include a non-zero frequency that can be at or can exceed at least one of a RF frequency or a microwave frequency.

Aspect 19 can include or use, or can optionally be combined with the subject matter of one or any combination of Aspects 1 through 18 to optionally include or use tuning an output impedance of an electrical energy signal generator, providing the time-varying electrical energy, such as to an impedance between the two or more electrodes at a frequency of the time-varying electrical energy generated by the electrical energy signal generator.

Aspect 20 can include or use, or can optionally be combined with the subject matter of one or any combination of Aspects 1 through 19 to optionally include or use the establishing or adjusting a temperature of the semiconductor substrate, including direct heating of the semiconductor substrate such as by an electric field produced by the time-varying electrical energy, such as without requiring indirect heat coupling to the substrate.

Aspect 21 can include or use, or can optionally be combined with the subject matter of one or any combination of Aspects 1 through 20 to optionally include or use, such as can comprise using temperature information such as from the temperature sensor such as to establish or adjust an amplitude of the time-varying electrical energy such as received by the two or more electrodes.

Aspect 22 can include or use, or can optionally be combined with the subject matter of one or any combination of Aspects 1 through 21 to optionally include or use temperature information, such as from the temperature sensor, such as to establish or adjust a frequency of the time-varying electrical energy such as received by the two or more electrodes.

Aspect 23 can include or use, or can optionally be combined with the subject matter of one or any combination of Aspects 1 through 22 to optionally include or use temperature information such as from the temperature sensor such as to adjust an impedance matching such as between an electric field signal generator circuit and an impedance between the two or more electrodes.

Aspect 24 can include or use, or can optionally be combined with the subject matter of one or any combination of Aspects 1 through 23 to optionally include or use temperature information such as from the temperature sensor such as to control extracting heat such as from the semiconductor substrate.

Aspect 25 can include or use subject matter (such as an apparatus, a system, a device, a method, a means for performing acts, or a device readable medium including instructions that, when performed by the device, can cause the device to perform acts), or can optionally be combined with the subject matter of one or any combination of Aspects 1 through 24 to optionally include or use or provide a substrate and one or more electrodes, located directly or indirectly on the substrate. The electrodes can be configured to receive a non-zero frequency time-varying electrical energy that can be coupled by the one or more electrodes to the substrate to trigger a current to generate frequency-controlled heat in the substrate. The heat generation can be controlled by adjusting the frequency of the time-varying electrical energy.

Aspect 26 can include or use, or can optionally be combined with the subject matter of one or any combination of Aspects 1 through 25 to optionally include or use the one or more electrodes including two or more electrodes including first and second electrodes separated from each other by different minimum spacing at different locations on at least one of the first and second electrodes so that adjusting the frequency of the time-varying electrical energy is capable of selectably adjusting at least one corresponding frequency-dependent current path between the first and second electrodes to provide the frequency-controlled heat at at least one desired location in the substrate.

Aspect 27 can include or use, or can optionally be combined with the subject matter of one or any combination of Aspects 1 through 26 to optionally include or use the substrate including a semiconductor substrate. The two or more electrodes can be capacitively coupled to the semiconductor substrate.

Aspect 28 can include or use, or can optionally be combined with the subject matter of one or any combination of Aspects 1 through 27 to optionally include or use a temperature sensor, which can be located in association with the substrate to sense a temperature associated with the substrate. An electric field signal generator circuit can be configured to generate the time-varying electrical energy. A control circuit can be configured to use temperature information from the temperature sensor to establish or adjust at least one of: (1) an amplitude of the time-varying electrical energy generated by the electric field signal generator; (2) a frequency of the time-varying electrical energy generated by the electric field generator; or (3) a location or distribution of a current path between the first and second electrodes.

Aspect 29 can include or use, or can optionally be combined with the subject matter of one or any combination of Aspects 1 through 28 to optionally include or use the two or more electrodes including first and second electric field nodes that can include, at a first location on the semiconductor substrate, a spacing separating the first and second electrodes. The spacing can be specified to be less than or equal to a spacing capable of generating heat in the semiconductor substrate, without requiring net charge flow into or out of the semiconductor substrate via pass-through conduction current, in response to the time-varying electrical energy received at the first and second electrodes.

Aspect 30 can include or use, or can optionally be combined with the subject matter of one or any combination of Aspects 1 through 29 to optionally include or use the one or more electrodes including electrically conductive material that can be separated from the substrate by a dielectric layer.

Aspect 31 can include or use, or can optionally be combined with the subject matter of one or any combination of Aspects 1 through 30 to optionally include or use the temperature of the substrate being adjustable by direct heating of the substrate by an electric field produced by the time-varying electrical energy, without requiring indirect heat coupling to the semiconductor substrate via the dielectric.

Aspect 32 can include or use, or can optionally be combined with the subject matter of one or any combination of Aspects 1 through 31 to optionally include or use an amplitude of the time-varying electrical energy received by the one or more electrodes being controlled using information about the temperature of the substrate to establish or adjust the temperature of the substrate.

Aspect 33 can include or use, or can optionally be combined with the subject matter of one or any combination of Aspects 1 through 32 to optionally include or use a frequency of the time-varying electrical energy received by the electrodes is controlled using information about the temperature of the substrate to establish or adjust the temperature of the substrate.

Aspect 34 can include or use, or can optionally be combined with the subject matter of one or any combination of Aspects 1 through 33 to optionally include or use the two or more electrodes include a first electrode that is located directly or indirectly on a first face of the semiconductor substrate and a second electrode that is located directly or indirectly an opposing second face of the semiconductor substrate.

Aspect 35 can include or use, or can optionally be combined with the subject matter of one or any combination of Aspects 1 through 34 to optionally include or use the second electrode covering enough of the opposing second face of the semiconductor substrate to form a ground plane with respect to the first electrode.

Aspect 36 can include or use, or can optionally be combined with the subject matter of one or any combination of Aspects 1 through 35 to optionally include or use the two or more electrodes including a first electrode comprising a linear trace that can be located directly or indirectly on a first face of the semiconductor substrate and a second electrode comprising a linear trace that can be located directly or indirectly on the first face of the semiconductor substrate and separated from the first electrode by a specified distance.

Aspect 37 can include or use, or can optionally be combined with the subject matter of one or any combination of Aspects 1 through 36 to optionally include or use the specified distance being fixed.

Aspect 38 can include or use, or can optionally be combined with the subject matter of one or any combination of Aspects 1 through 36 to optionally include or use the specified distance varying to form a tapered or diverging or serpentine arrangement.

Aspect 39 can include or use, or can optionally be combined with the subject matter of one or any combination of Aspects 1 through 38 to optionally include or use a ground plane located on an opposing second face of the semiconductor substrate at a specified distance from the first and second electrodes.

Aspect 40 can include or use subject matter (such as an apparatus, a system, a device, a method, a means for performing acts, or a device readable medium including instructions that, when performed by the device, can cause the device to perform acts), or can optionally be combined with the subject matter of one or any combination of Aspects 1 through 39 to optionally include or use or provide a method of establishing or adjusting a temperature of a heating element. The subject matter can comprise obtaining or providing a substrate and one or more electrodes, which can be located directly or indirectly on the substrate. A non-zero frequency time-varying electrical energy can be received at the one or more electrodes. The time-varying electrical energy can be controlled to trigger a current to generate frequency-controlled heat in the substrate. A temperature of the substrate can be established or adjusted. This can include controlling the frequency of the electrical energy received at the one or more electrodes.

Aspect 41 can include or use, or can optionally be combined with the subject matter of one or any combination of Aspects 1 through 40 to optionally include or use the obtaining or providing a substrate and one or more electrodes comprising obtaining or providing two or more electrodes including first and second electrodes separated from each other by different minimum spacing at different locations on at least one of the first and second electrodes. The frequency of the time-varying electrical energy can be adjusted for selectably adjusting at least one corresponding frequency-dependent current path between the first and second electrodes to provide the frequency-controlled heat at at least one desired location in the substrate.

Aspect 42 can include or use, or can optionally be combined with the subject matter of one or any combination of Aspects 1 through 41 to optionally include or use capacitively coupling the time-varying electrical energy from the one or more electrodes to the substrate.

Aspect 43 can include or use, or can optionally be combined with the subject matter of one or any combination of Aspects 1 through 42 to comprise wirelessly receiving, at the one or more electrodes, time-varying electrical energy that includes a non-zero frequency that is at or exceeds at least one of a RF frequency or a microwave frequency.

Aspect 44 can include or use, or can optionally be combined with the subject matter of one or any combination of Aspects 1 through 43 to comprise sensing a temperature associated with the substrate and, using information about the sensed temperature, establishing or adjusting at least one of (1) an amplitude of the time-varying electrical energy generated by the electric field signal generator; (2) a frequency of the time-varying electrical energy generated by the electric field generator; or (3) a location or distribution of a current path between the first and second electrodes.

Aspect 45 can include or use, or can optionally be combined with the subject matter of one or any combination of Aspects 1 through 44 such that the two or more electrodes include first and second electric field nodes that can include, at a first location on the semiconductor substrate, a spacing separating the first and second electrodes, wherein the spacing can be specified to be less than or equal to a spacing capable of generating heat in the semiconductor substrate, without requiring net charge flow into or out of the semiconductor substrate via pass-through conduction current, in response to the time-varying electrical energy received at the first and second electrodes.

Aspect 46 can include or use, or can optionally be combined with the subject matter of one or any combination of Aspects 1 through 45 to include or use establishing or adjusting a temperature of the substrate, including direct heating of the substrate by an electric field produced by the time-varying electrical energy, without requiring indirect heat coupling to the substrate.

Aspect 47 can include or use, or can optionally be combined with the subject matter of one or any combination of Aspects 1 through 46 to include or use temperature information to establish or adjust an amplitude of the time-varying electrical energy received by the two or more electrodes.

Aspect 48 can include or use, or can optionally be combined with the subject matter of one or any combination of Aspects 1 through 47 to include or use temperature information to establish or adjust a frequency of the time-varying electrical energy received by the two or more electrodes.

Aspect 49 can include or use, or can optionally be combined with the subject matter of one or any combination of Aspects 1 through 47 to include or use temperature information to establish or adjust an impedance matching between an electric field signal generator circuit and an impedance between the two or more electrodes.

Aspect 50 can include or use, or can optionally be combined with the subject matter of one or any combination of Aspects 1 through 49 to include or use temperature information to control extracting heat from the substrate.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIGS. 8A, 8B, 8C, 8D, 8E, and 8F show various arrangements of various substrates, electrodes, and insulators.

DETAILED DESCRIPTION

Figure 1:
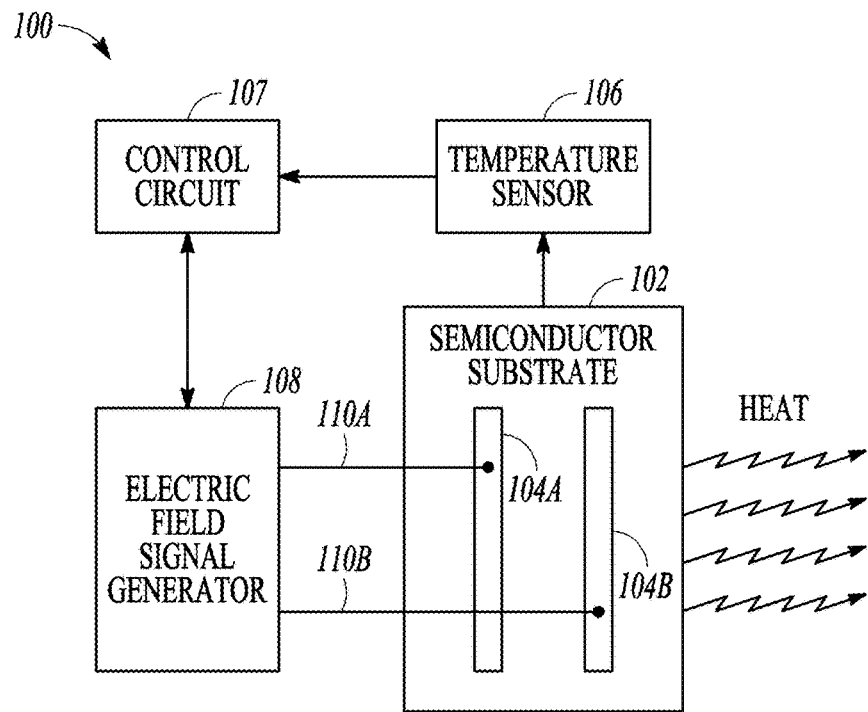
FIG. 1 shows an example of a heating or other temperature adjustment system.

This document describes examples of improved techniques for establishing or adjusting temperature of a semiconductor or other suitable substrate (or, indirectly, that of an object or space that is thermally coupled to the substrate) such as for establishing or adjusting one or more temperature gradients in the substrate.

In an illustrative, non-limiting example, the present techniques can turn a semiconductor substrate into a heat source, such as by capacitively applying a radiofrequency (RF) or microwave or other time-varying frequency source as the input energy. This can permit localized heat production, controllably variable heat production, multi-mode control of the localized heat production, and efficient heat generation. Localized heating can further enable establishing and managing one or more temperature gradients in the substrate, such as in time or space, or both.

The present techniques can use a semiconductor substrate, or one or more other materials with free charge carriers that can remain confined within the substrate, for producing thermal energy—which is different from the waste thermal energy produced by a typical semiconductor logic or other integrated circuit chip, which requires pass-through current.

For example, unlike a digital or analog semiconductor integrated circuit, the present localized heat generation apparatus and methods need not require an electrically conductive connection to power and ground, although such power and ground inputs can be included for use with other electrical circuits that can optionally be included on the same integrated circuit as the present localized heat generation apparatus. By contrast, a typical digital or analog semiconductor integrated circuit will require logic gate circuits and electrically conductive power and ground connections.

In an example of using the present techniques, the RF or other time-varying frequency energy can be transferred to the semiconductor or other substrate through capacitive contacts (in an illustrative non-limiting example). The resulting process can be conceptualized as an input conduction current, which leads to a displacement current in the first capacitive electrode contact, and conduction current in the substrate, a displacement current in the second capacitive electrode contact, and finally a conduction current out of the second electrode to the voltage source. Displacement current is only generated at the capacitor contacts when an alternating voltage of nonzero frequency is applied. An oscillating conduction current in the substrate is created when the excitation is an alternating voltage of nonzero frequency. When viewed from a particle physics perspective, the charged particles in the substrate are confined to the body of the substrate and do not physically leave the substrate through the capacitive contacts. The continuity condition for current means that the displacement current in the capacitor is equal to the conduction current in the substrate. In the present approach, when using a semiconductor substrate, heat is generated by inelastic collision of the majority carriers confined within the semiconductor substrate with the semiconductor lattice and heat conduction is by the semiconductor lattice. In the present approach, when using a thin-film metal or other substrate, the heat is carried by majority carriers moving in the thin film metal or other substrate.

The present techniques can allow multi-mode control of thermal energy production and the establishment of one or more thermal gradients at desired locations in the substrate. Thermal energy production in the semiconductor material can be accomplished by altering energy input of the time-varying electric field. In a first mode, this can be achieved by specifying or managing the spacing between electrodes, and/or managing the inductance between the electrodes either by tuning the spacing or through external circuits connected to the electrodes that can be used to capacitively apply a time-varying frequency to the semiconductor. A second mode can control thermal energy production by establishing or adjusting the frequency of the time-varying electrical signal that is capacitively or otherwise applied to the semiconductor or other substrate. A third mode can control thermal energy production by adjusting the amplitude of the time-varying electrical signal that is capacitively or otherwise applied to the semiconductor or other material. Two or more of these modes can be used in combination with each other, or with one or more other adjunct modes.

One or more thermal energy gradients can be established in the semiconductor substrate using one or multiple techniques. For example, adjusting the frequency of the time-varying electrical signal being capacitively or otherwise applied to the semiconductor or other substrate via the electrodes can change a matching or coupling efficiency using such electrodes, which, in turn, can establish or control one or more thermal gradients. The "match" between the applied time-varying electrical signal and the electrodes is a function of both the frequency of the applied time-varying electrical signal and the spacing between electrodes at one or more locations on such electrodes. Variable thermal energy production with a particular pair of electrodes can be used to establish or adjust a localized thermal energy gradient in the semiconductor substrate, such as by specifying or adjusting a spacing between the electrodes (or respective nearest or other portions thereof) being used to capacitively input the time-varying electrical signal. Variation in spacing between locations on respective electrodes can be used to create a variable frequency match, for a particular input frequency, such as along the axis or length of the electrodes (see, e.g., spacing "S" and axis "Y" in FIGS. 6-7). This can provide variable energy deposition along the axis of the electrodes and, consequentially, a temperature gradient along the axis of the electrodes.

Once the electrodes are in place, the spacing or geometry will remain constant. Further control of the temperature gradient can be established by altering the frequency of the time-varying electrical signal being applied to the electrodes. The temperature gradient is a consequence of a distribution of thermal energy bands, and associated underlying current bands, between the electrodes or between respective locations on the respective electrodes.

Figure 9A:
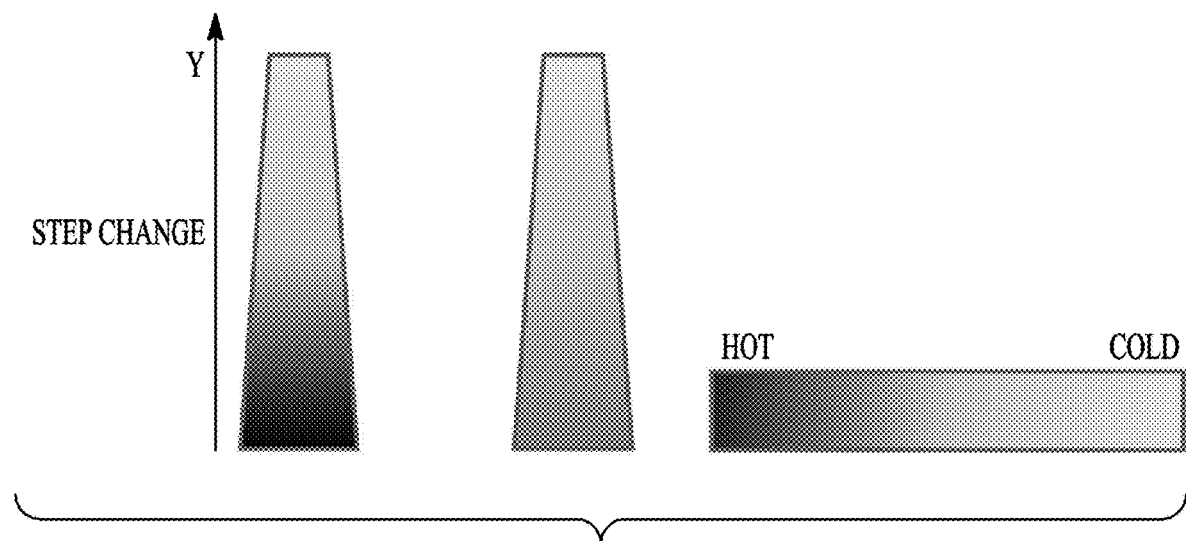
FIG. 9A illustrates an example of changing a frequency of an applied electrical signal to obtain "step function" control of a localized spatial temperature gradient.

In an example, a frequency change of the applied electrical energy can create a "step function" in the temperature gradient, in which the overall spatial temperature gradient can remain the same in response to the frequency change, but in which the temperature values of the maximum and minimum temperatures in the spatial temperature gradient change in response to the change in the applied frequency. The step function in the spatial temperature gradient can match to the average or lumped impedance between the traces or electrodes, which can be treated as a single lumped system. In a serpentine or variable-spacing electrode geometry, it is possible that certain locations on the electrode get "turned off," because no match exists at the applied frequency for such locations, therefore, no current or heat is generated at such locations. FIG. 9A illustrates an example of step function control.

Figure 9B:
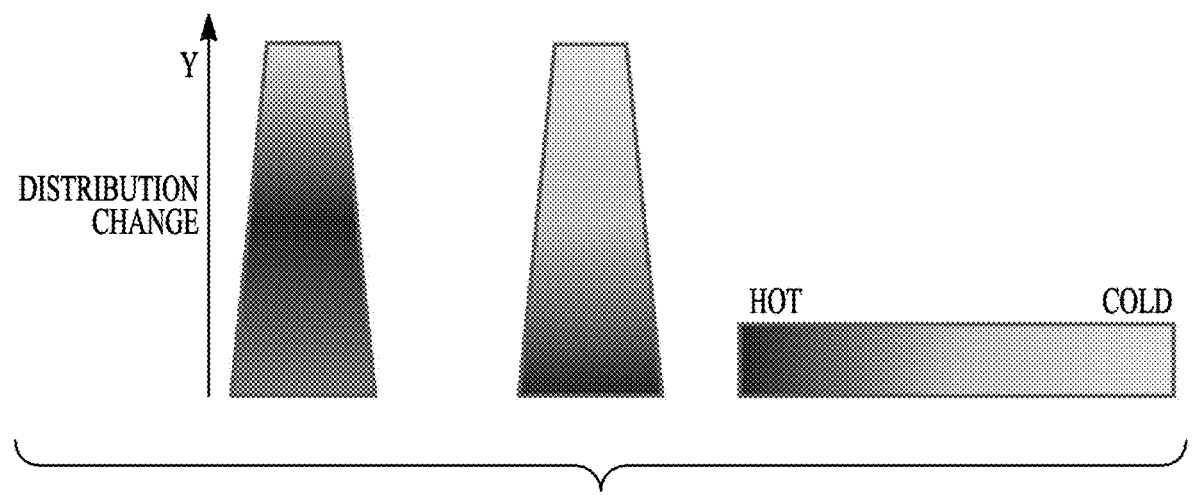
FIG. 9B illustrates an example of changing a frequency of an applied electrical signal for altering a spatial distribution of the temperature gradient, such as can include altering the locations of the maximum and minimum temperatures by shifting along the Y-axis.

In an example, a frequency change of the applied electrical energy can additionally or alternatively alter the spatial temperature gradient by altering the spatial distribution of the thermal and underlying current bands between respective locations on the respective electrodes. In an example, such altering the spatial distribution of the temperature gradient can include altering the locations of the maximum and minimum temperatures, e.g., shifting along the Y-axis. FIG. 9B illustrates an example of such a frequency change altering a spatial distribution of the temperature gradient, such as can include altering the locations of the maximum and minimum temperatures by shifting along the Y-axis. Without being bound by theory, it is believed, based on current theory and similar applications, that frequency control may be capable of controlling the match at individual points of the electrodes along the Y-axis.

The ability to establish spatial temperature gradient variations can be desirable for certain applications. Depending on the geometry and size of the electrodes, it may not be always be possible to recognize the minute changes in spatial temperature gradients, making step function control preferred as a practical way to adjust or control such temperature gradients.

In the third technique, the frequency of the time-varying electrical input signal can be altered, such as to enable a partial impedance match the between the electrodes to obtain the requisite energy input for obtaining the desired localized thermal energy output in the substrate. In sum, multi-modal control of localized and variable thermal energy production in the semiconductor substrate is possible.

The present approach to localized heating is believed to be more efficient than heating a semiconductor within a microwave cavity. In cavity heating efficiency depends on the ratio of the size of the cavity and the target semiconductor. By contrast, the present approach requires no cavity and offers a way to access the semiconductor continuously, such as for using the semiconductor as an active heat source, rather than just a target object to be heated.

FIG. 1 shows an example of a heating or other temperature adjustment system 100. In an example, the system 100 can include a silicon, germanium, gallium arsenide or other semiconductor substrate 102 (or other non-semiconductor substrate material, as explained elsewhere herein). The semiconductor substrate 102 can include one or more of a bulk semiconductor, a semiconductor wafer, a diced or other portion of a semiconductor wafer, etc.

Two or more electrodes 104A-B can be located indirectly on the semiconductor substrate 102. The electrodes 104A-B can be located so as to be physically separated from each other. Such separation can include a region of the semiconductor substrate 102 generally located at least partially between the electrodes 104A-B. In an example, the electrodes 104A-B can include metal or other electrically conductive signal traces. Such conductive signal traces can be indirectly located on the semiconductor substrate 102, for example, such as separated therefrom by an intervening insulator or dielectric layer, such as silicon dioxide, silicon nitride, or the like. Such separation from the semiconductor substrate 102 by an intervening dielectric layer can permit, in an example, capacitive coupling of a non-zero frequency time-varying electric field signal on the electrodes 104A-B to the semiconductor substrate 102. The electrodes 104A-B can be configured to receive the time-varying electrical energy, such as can include an externally regulated and applied non-zero frequency, such as for creating a resulting time-varying electric field in the semiconductor substrate 102, such as for establishing or adjusting a local temperature of the portion of the semiconductor substrate 102 that is located in a vicinity between or near the electrodes 104A-B.

A temperature sensor 106 can be integrated into, formed upon, placed near, or otherwise located in association with the semiconductor substrate 102 or an object or space to be heated by the semiconductor substrate, such as to sense a temperature thereof. Information representative of the temperature of the semiconductor substrate 102 can be provided by the temperature sensor 106, such as to a control circuit 107. The control circuit 107 can be configured to control an electric field signal generator 108, such as for use in closed-loop or other control of the frequency, amplitude, or other operation of the electric field signal generator 108. In an illustrative example, the temperature sensor 106 can include a pn junction diode integrated into the semiconductor substrate 102. This can provide a resulting temperature-dependent reverse-bias pn junction diode current signal. This resulting signal can be signal-processed, such as by the control circuit 107, such as to provide a resulting temperature-dependent control signal to the electric field signal generator 108, such for use to adjust an output frequency or amplitude or impedance matching of the electric field signal generator 108, such as to establish or adjust a temperature of the semiconductor substrate 102 or a localized portion thereof.

The electric field signal generator 108 can include a signal generator (source) and can optionally include an impedance matching circuit. The electric field signal generator 108 can be operatively coupled to the electrodes 104A-B, such as by using a wired or at least partly wireless connection 110A-B, such as to deliver a time-varying electric field signal to the electrodes 104A-B. The time-varying electric field signal received by the electrodes 104A-B from the electric field signal generator 108 can be used to apply an AC electric field, e.g., a time-varying electric field having non-zero frequency, to a portion of the semiconductor substrate 102, such as to provide a resulting displacement current to the portion of the semiconductor substrate 102, such as to trigger heating or otherwise establish or adjust a temperature of the portion of the semiconductor substrate 102, and without requiring indirect heat coupling passing heat through the dielectric to the semiconductor substrate 102.

Heating the semiconductor substrate 102 by localized capacitively-coupled application of a non-zero frequency time-varying electric field does not require a net charge flowing into or out of the semiconductor substrate. Without being bound by theory, it is believed that the present approach of applying non-zero frequency time-varying electric field can induce particle motion such that majority carriers in the semiconductor substrate 102 can oscillate bidirectionally (e.g., back-and-forth) at the applied frequency with respect to the lattice of the semiconductor substrate. This is believed to produce phonons that vibrate periodically in harmonic motion proportional to the oscillating displacement current. By controlling the frequency of the non-zero frequency applied time-varying electric field, the majority carrier oscillation can be controlled which, in turn, can control phonons and heat generation.

Such heating the semiconductor substrate 102 using the displacement current by the present approach of applying a non-zero frequency time-varying electric field is also different from inductive heating in that, unlike inductive heating, no magnetic field need be applied. No magnetic-field induced eddy currents in the semiconductor substrate 102 need be created. No loop or electromagnet is required to establish a magnetic field in the semiconductor substrate.

Information about the temperature of the semiconductor substrate 102, such as sensed by the temperature sensor 106, can be used to control at least one of the amplitude or the frequency of the electric field generated by the electric field signal generator 108 and provided by the electrodes 104A-B to the semiconductor substrate 102, and can additionally or alternatively be used to turn the applied electric field on or off, such as at a desired duty cycle to attain or maintain a target temperature of the semiconductor substrate 102, or a target temperature of an object or space to be heated by the semiconductor substrate 102.

Adjusting the non-zero frequency of the applied time-varying electric field can affect a coupling of the time-varying electric field to the semiconductor substrate 102 and, therefore, can be used to control the conversion of the applied electric field into heating of the semiconductor substrate 102. The applied frequency manifests itself as the oscillating frequency of the particles inside the substrate. The applied frequency can range (e.g., depending on the application) such as all the way from a low frequency, for example, such as near-DC, a 60 Hz line frequency, up to a frequency in a radio frequency (RF) or microwave or TeraHertz (THz) frequency range, or beyond. Additionally or alternatively, adjusting the amplitude of the applied electric field can affect the power of the electric field to the semiconductor substrate 102 and, therefore, can be used to control the conversion of the applied electric field into heating of the semiconductor substrate 102. Additionally or alternatively, one or more constructive or destructive interference or duty cycle or other technique can be used, such as to control an amplitude of the applied non-zero electric field at a desired location or region of the semiconductor substrate 102.

In an example, the two or more electrodes 104A-B shown in FIG. 1 can include parallel straight linear metal strip segments, such as can be located on the same side of the bulk semiconductor substrate 102, but separated therefrom by a silicon dioxide, silicon nitride, polytetrafluoroethylene, or other insulating dielectric layer. Such strips can be separated from each other by a spacing that is small enough to be capable of generating heat in the semiconductor substrate 102 in response to the displacement current provided by the non-zero frequency applied electric field. The exact spacing for such heat generation may depend on the type of material of the semiconductor substrate 102, the type or amount of doping of the semiconductor substrate 102, the type or thickness of the insulator, the applied amplitude and frequency of the non-zero frequency applied time-varying electric field.

Moreover, the two or more electrodes 104A-B need not be located on the same side of the semiconductor substrate 102. In an example, at least one of the two or more electrodes 104A-B can be located on an opposing side of the semiconductor substrate 102 from at least one other of the two or more electrodes 104A-B. For example, the two or more electrodes 104A-B can be located on the same side of the semiconductor substrate, with a further electrode 104 on the opposite side of the semiconductor substrate 102, such as can be wider, e.g., to form a ground plane. Such an approach can be useful, for example, in a balanced line excitation approach, with V+ and V− applied to the two signal traces on the same side of the semiconductor substrate 102, with respect to a ground plane, such as can be electrically connected to a ground or other reference voltage, on an opposing side of the semiconductor substrate 102.

Additionally or alternatively, the two or more electrodes 104A-B can have a tapered or variable spacing from each other, rather than the fixed spacing shown in the parallel example of FIG. 1. For example, the electrodes 104A-B can include segments that are separated from each other, but arranged with respect to each other at a 45 degree or other angle, such as diverging to form a "V" but without touching each other. As explained herein, the frequency of the applied electrical signal can be adjusted to shift the location of one or more current paths between the electrodes, such as to a location at which the spacing between the electrodes provides a certain match to the frequency. In a non-tapered example (e.g., parallel electrodes with the same spacing therebetween at all locations on the electrodes), the frequency of the applied electrical signal can be adjusted to increase or decrease the amount of heat generated by the resulting current flowing between the electrodes.

In various examples, the length of the conductive segments of the electrodes 104A-B can extend completely across the semiconductor substrate 102, or can extend for a fraction of that distance, such as until all of the non-zero frequency applied electric field signal is absorbed by the semiconductor substrate 102.

The line impedance presented the at least two electrodes 104A-B and the semiconductor substrate 102 region therebetween (e.g., with or without a ground plane on the opposing side of the semiconductor substrate 102) can be determined by calculation or measurement. An impedance matching circuit can be included between the electric field signal generator 108 and the electrodes 104A-B, such as to increase or maximize power transfer therebetween. The impedance matching circuit can include a narrow bandwidth or other impedance matching circuit that can be configured to match, e.g., at a specified frequency of the time-varying electric field signal generator 108, the line impedance presented by the two or more electrodes and the output impedance of the electric field signal generator 108. Such an approach can enable creation of a desired match without the need to adjust frequency. It can be especially useful when a fixed frequency source is the only available source.

Figure 2:
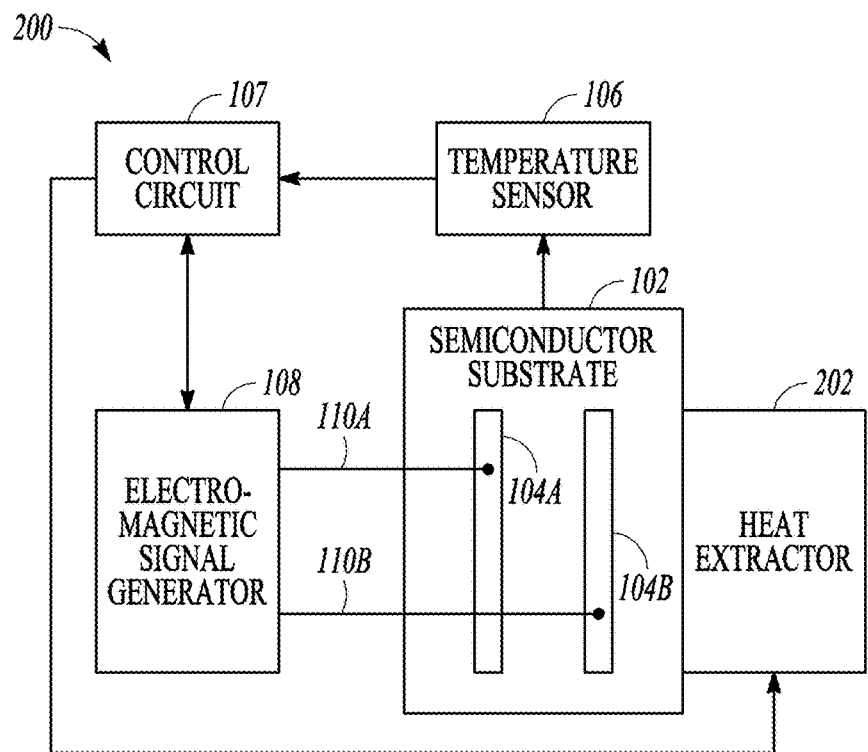
FIG. 2 shows an example of a system, similar to that shown in FIG. 1, that can optionally include a passive or active heat extractor.

FIG. 2 shows an example of the system 200 that can optionally include a passive or active heat extractor 202. The heat extractor 202 can be coupled to one or more instances of the semiconductor substrate 102 (or one or more localized regions of the one or more instances of the semiconductor substrate 102). The heat extractor 202 is one example of how to establish or optimize a thermal extraction energy pathway, such as to help extract heat from the semiconductor substrate 102. The extracted thermal energy can be transferred elsewhere, such as to a target object or space. An example of a passive heat extractor 202 can include a heat sink. The heat sink can be selected to have good thermal conductivity, for example, higher thermal conductivity than that of the semiconductor substrate 102. The heat sink can be integrated with the semiconductor substrate, for example, by including metal or other thermally conductive regions on or in the substrate. The heat sink can be configured with one or more heat dispersion structures, such as one or more of one or more cooling fins such as can permit radiation or convection of heat such as away from the semiconductor substrate 102 or toward a target object or space. The heat sink can be configured with one or more fluid channels, such as can allow liquid or other fluid flow or transport therein, such as in a partially or fully contained manner, such as in a fluid flow circuit. An active heat sink can include a fan, pump, or other active device, such as to encourage heat flow away from the semiconductor substrate 102. In an example, the heat extractor 202 can be controlled by a signal provided by the control circuit 107, such as based on information from the temperature sensor 106 about the temperature of the semiconductor substrate 102 or about the target object or area or about the heat extractor 202 itself, depending on the selected one or more locations of one or more instances of the temperature sensor 106.

Figure 4:
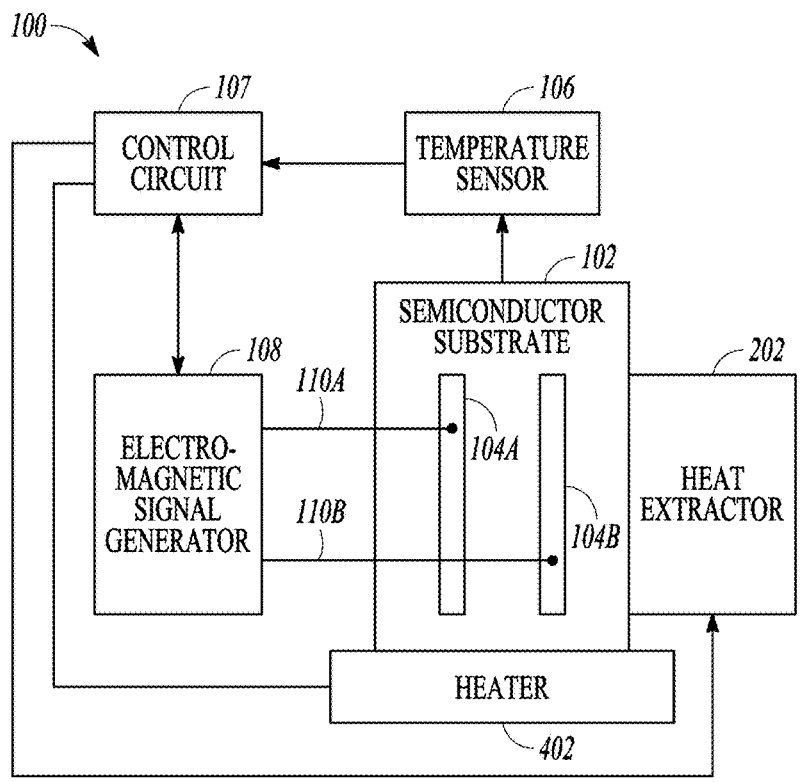
FIG. 4 shows an example, similar to FIGS. 1 and 2, including an optional biasing heater, such as can be used to pre-heat the substrate, such as to a desired temperature.

FIG. 4 shows an example, similar to FIGS. 1 and 2, including an optional biasing heater 402, such as can be used to pre-heat the semiconductor substrate 102, such as to a desired temperature, such as at or just below what can be referred to as an atomic thermal equilibrium (ATE) temperature. Without being bound by theory, at the ATE temperature, it may be easier for the applied non-zero electric field to excite the majority carriers in the semiconductor substrate into oscillation with the semiconductor substrate to efficiently generate further thermal energy. The biasing heater 402 can include an electric or gas-fueled heater, or a magnetic induction heater that can include a loop or electromagnet to create eddy currents in the semiconductor substrate 102 to pre-heat the semiconductor substrate 102 to ATE for then applying the non-zero frequency time-varying electric field for generating further thermal energy in the semiconductor substrate 102.

The biasing heater 402 can be omitted, and the system 100 can be controlled by the temperature sensor 106 and the control circuit 107 to operate at or near such an ATE temperature. For example, the heat extractor 202 can include an active heat extractor that can be controlled (e.g., in a closed-loop negative feedback arrangement) such as to extract thermal energy from the semiconductor substrate 102 at a rate that maintains a temperature of the semiconductor substrate 102 or near an ATE temperature or other temperature at which further thermal energy can be efficiently or most efficiently generated from the semiconductor substrate 102.

Figure 5:
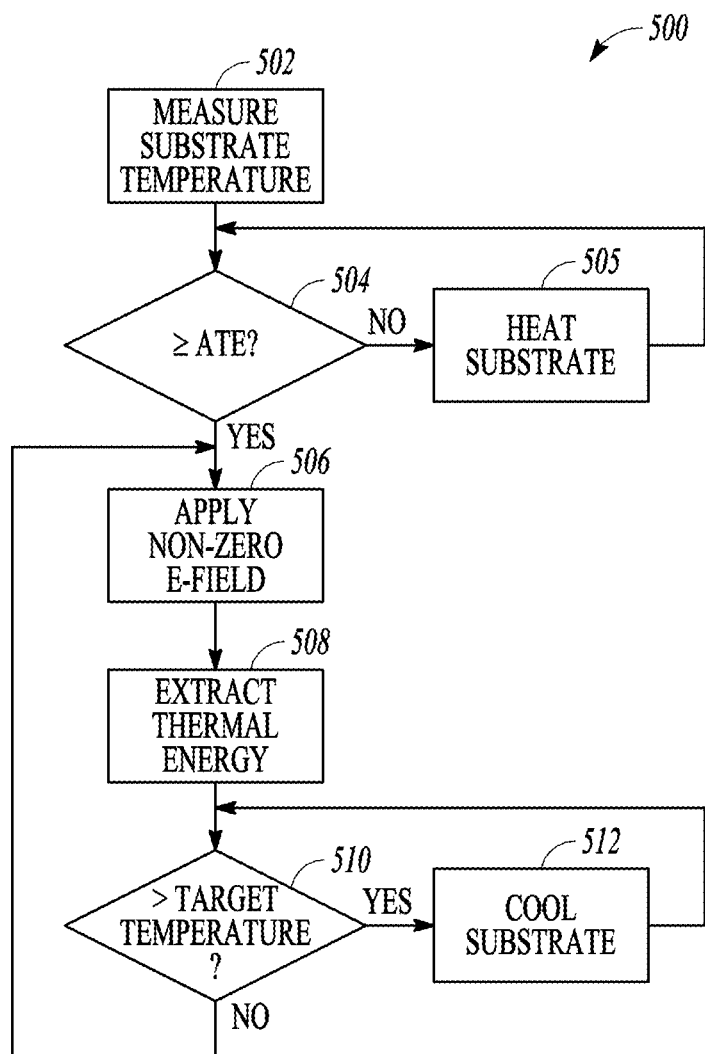
FIG. 5 shows an example of a method of operating one or more of the systems, or portions thereof, such shown in FIGS. 1-2, and 4.

FIG. 5 shows an example of a method 500 of operating one or more of the systems, or portions thereof, such shown in FIGS. 1-4. At 502, a temperature of the semiconductor substrate 102 (or object or space to be heated by the semiconductor substrate) can be measured. At 504, the measured temperature can be compared to a specified expected ATE temperature of the semiconductor substrate 502. If the measured temperature is not at or above the expected ATE temperature, then at 505, the semiconductor substrate 102 can be heated, and the temperature can be re-measured at 504. Otherwise, at 504, if the measured temperature is at or above the ATE temperature, a non-zero frequency time-varying electric field can be applied to the semiconductor substrate 102, such as by the local electrodes that can be located on the semiconductor substrate 102, such as separated therefrom by a dielectric layer. A frequency or amplitude of the non-zero frequency time-varying electric field can be controlled, such as to obtain a desired degree of majority-carrier oscillation induced harmonic vibration of the lattice of the semiconductor substrate, thereby generating thermal energy in the semiconductor substrate. At 508, thermal energy can be actively or passively extracted from the semiconductor substrate, such as for heating a target object or space. In an example, such thermal energy extraction at 508 can include thermoelectric cooling of the semiconductor substrate 102. At 510, a temperature of the semiconductor substrate can be measured. If the measured temperature exceeds a target temperature, e.g., of the semiconductor substrate 102, or of an object or space to be heated by the semiconductor substrate 102, then at 512, the semiconductor substrate 102' (or the target object or space) can be cooled, such as by an thermoelectric cooling device that can be integrated into the semiconductor substrate 102. Otherwise, at 510, if the temperature of the semiconductor substrate 102 (or the target object or space) is not at the target temperature, then the non-zero frequency time-varying electric field application can continue at 506. When a desired amount of heat has been extracted, or when a temperature of the target object or space has been increased to be at or above a target temperature, then the method of 500 can be paused or can terminate.

Figure 3:
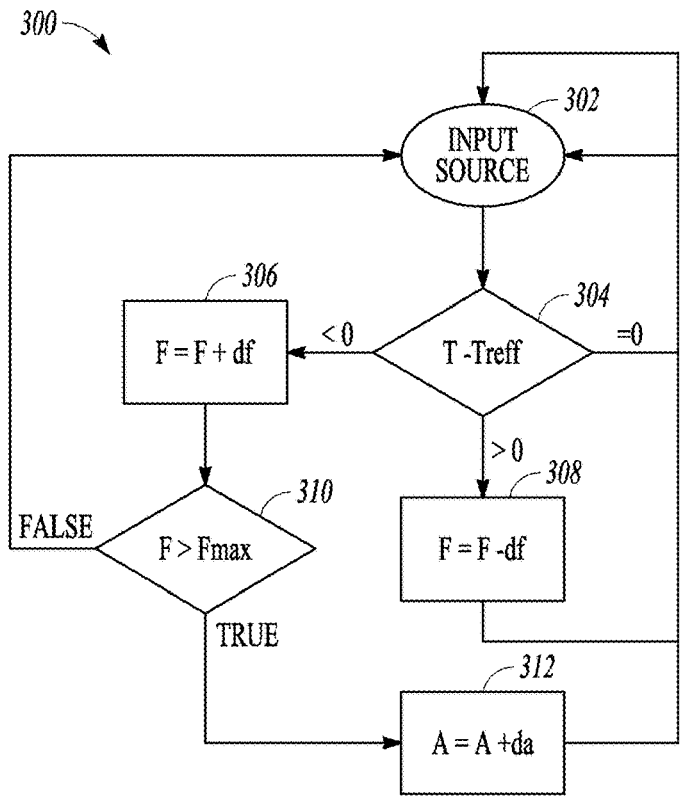
FIG. 3 shows an example of a method of operating one or more of the systems, or portions thereof, such as shown in FIGS. 1-2, and 4.

FIG. 3 shows an example of a method 300 of operating of operating one or more of the systems, or portions thereof, such shown in FIGS. 1,2 and 4. At 302, an electromagnetic signal generator 108 can output a time-varying signal of amplitude A and frequency F, which can be capacitively applied to the semiconductor substrate 102, such as explained elsewhere in this document. At 304, a temperature T of the substrate 102, such as can be measured by the temperature sensor 106, can be provided to the control circuit 107, which at 304 can compare the measured temperature T to a desired or reference temperature Treff. If the measured temperature T is less than the reference temperature Treff, then process flow can proceed to 306. If the measured temperature T is greater than the reference temperature Treff, then process flow can proceed to 308. If the measured temperature T is equal to the reference temperature Treff, then process flow can return to 302. Hysteresis can be used in the comparison, if desired.

At 306 (Treff>T), the frequency F can be increased by a specified incremental amount df. Then, at 310, the frequency F can be compared to a maximum frequency limit Fmax. At 310, if the incremented frequency F does not exceed F max, then process flow can return to 302. Otherwise, if the incremented frequency F exceeds Fmax, then the frequency F can be limited at Fmax and process flow can continue to 312, and amplitude A can be increased by an incremental amount da, before the process flow returns to 302. A maximum permissible amplitude limit can be used, similar to the maximum frequency limit described.

In an example, the control circuit 107 (or other control device) can control the temperature, such as by establishing or adjusting Treff, such as to a specified fixed or variable value such as depending on the need for heat generation.

Although the present patent application has focused on using a semiconductor substrate, to which a time-varying electrical signal can be capacitively applied to generate heat in the semiconductor substrate, the present subject matter is not so limited. Instead of (or in addition to) the semiconductor substrate, a thin-film metal substrate material (or any other material that can provide free charged particles) can be used, with a time-varying electrical signal capacitively coupled thereto. The capacitive contacts can isolate the substrate. The associated dielectric isolation between the input signal and the substrate can inhibit or prevent a short-circuit through the substrate or other similar effects. Such dielectric isolation can also help enable use of the present techniques in applications such as in which a fire or other consequence of an electrical current short-circuit may be of concern.

One structure suitable for capacitively applying a time-varying electrical signal to a semiconductor or other substrate with electrical charged particle carriers that are free to move within the substrate, can include a pair of parallel linear signal traces, each of length L in a direction y, and separated from each other by a separation distance s, and isolated from a first side of the substrate by a dielectric layer of thickness t, with a conductive ground plane on the opposing second side of the substrate. For such a structure, the line impedance (with or without the ground plane) can be determined by calculation and confirmed by measurement. An example of appropriate calculations is described below.

For a substrate without a ground plane, using a conformal transformation and the Schwartz-Christofel transformation, it can be shown that the capacitance and conductance of an infinitely thick substrate for the parallel trace structure can be given by the equations below, neglecting the skin effect. In Equation 1, $C_1$=the capacitance in air per unit length. In Equation 2, $C_2$=the capacitance of the electrodes due to the substrate, per unit length. In Equation 3, these capacitances $C_1$ and $C_2$ add to give the total capacitance, per unit length. G=the conductance of the parallel trace structure, per unit length.

$$C_1 = \frac{\epsilon_0 K'(k_1)}{2K(k_1)} \quad \text{Eq. 1}$$

$$C_2 = \frac{\epsilon_0 \epsilon_r K'(k_1)}{2K(k_1)} \quad \text{Eq. 2}$$

$$C_{total} = C_1 + C_2 \quad \text{Eq. 3}$$

In Equations (1)-(3), $$k_1 = \frac{s}{s+2\omega} \quad \text{Eq. 4}$$

$K(k_1)$ is the complete elliptic integral of the first kind, and $K'(k_1)$
Note that:

$$K'(k_1) = K(k_1') \quad \text{Eq. 5}$$

Where $$k_1' = \sqrt{1-k_1^2} \quad \text{Eq. 6}$$

The substrate permittivity is given as $$\epsilon_s = \epsilon_0 \epsilon_r \quad \text{Eq. 7}$$

However, this expression may be complex due to its conductivity $$\sigma S/m \quad \text{Eq. 8}$$

In this case, the substrate permittivity becomes $$\epsilon_s = \epsilon_0 \left( \epsilon_r - \frac{J\sigma}{\omega \epsilon_0} \right) \quad \text{Eq. 9}$$

where ω is the angular frequency 2πf and f is the frequency of operation. Then, the expressions for $C_2$ and $C_{total}$ become complex and the imaginary term is G, the conductance per unit length. If the operating frequency f is zero, then the conductance G becomes $$G = \sigma K'(k_1)/2K(k_1) \quad \text{Eq. 10}$$

In Siemens per unit length. Also, note that if the substrate is absent, then $$C_{total-air} = 2C_1. \quad \text{Eq. 11}$$

The effective relative permittivity is the ratio of the capacitance of the structure with the substrate to the capacitance without the substrate, e.g., the capacitance in free space. The time-varying frequency guided by the electrodes will have a wave velocity given by the ratio of c (the velocity of light in free space) and the square root of the effective relative permittivity, that is:

$$c/\sqrt{\epsilon_{reff}} \quad \text{Eq. 12}$$

provided that the substrate is non-magnetic, with a permeability of $\mu_o$. Thus, the effective relative permittivity becomes $$\epsilon_{reff} = \frac{C_{total}}{C_{total-air}} = \frac{C_1+C_2}{2C_1} = \frac{(\epsilon_r+1)}{2} \quad \text{Eq. 13}$$

The time-varying electromagnetic wave will propagate supported by the electrodes and the substrate as:

$$\exp(J\omega t - \gamma y) \quad \text{Eq. 14}$$

in the y-direction, where $$\gamma = J\omega\sqrt{\mu_0 \epsilon_0 \epsilon_{reff}} \quad \text{Eq. 15}$$

If the wave propagation is lossless, when $\epsilon_r$ is real, then γ=jβ, where β is in radians/meter, and the electromagnetic wave propagates along the electrodes as:

$$J\beta = \frac{J\omega\sqrt{\epsilon_{reff}}}{C} \quad \text{Eq. 16}$$

where $$C = 1/\sqrt{\mu_0 \epsilon_0} \quad \text{Eq. 17}$$

is the velocity of light in free space. If $C_2$ is complex, then $\epsilon_{reff}$ is complex, γ=α+jβ, and the attenuation term α is the real part in amperes/meter. It becomes possible to design the structure so that all of the time-varying electromagnetic power on the electrodes has dissipated into the semiconductor substrate by the time that it has traversed the electrode length L and reached the end. The line impedance becomes:

$$Z_0 = \frac{120\pi K(k_1)}{\sqrt{\epsilon_{reff}} \, K'(k_1)} \qquad \text{Eq. 18}$$

When $\varepsilon_{reff}$ is complex, then the line impedance is also complex. Matching into the electrodes is possible with a careful design of the matching structure, such as can include using Eq. 18.

Finite Thickness Substrate

When the semiconductor substrate is of a finite thickness h, the equations can be slightly modified. The air capacitance term is identical to that previously presented. However, the substrate capacitance $C_2$ is now changed to:

$$C^s = \frac{\epsilon_0 \, (\epsilon_r - 1) K'(k_{10})}{2 K(k_{10})} \qquad \text{Eq. 19}$$

where $$k_{10} = \tanh\left(\frac{\pi s}{4h}\right) \Big/ \tanh\left(\frac{\pi(2\omega + s)}{4h}\right) \qquad \text{Eq. 20}$$

Thus, the effective relative permittivity becomes:

$$\epsilon_{reff} = \frac{C^a + C^s}{2 C^a} = \frac{1}{2}\left(1 + \frac{(\epsilon_r - 1) K'(k_{10}) K(k_1)}{K(k_{10}) K'(k_1)}\right) \qquad \text{Eq. 21}$$

The propagation constant $\gamma$ in radians/meter, of the electromagnetic wave along the electrodes is given as:

$$\gamma = \frac{J\omega \sqrt{\frac{C^a + C^s}{2 C^a}}}{c} = \frac{J\omega \sqrt{\epsilon_{reff}}}{c} \qquad \text{Eq. 22}$$

Where c is the velocity of light in free space. If $C^S$ is complex, then $\gamma$ has an attenuation term, which is the imaginary part. It becomes possible to design the structure so that all the time-varying electromagnetic power on the electrodes has dissipated into the substrate at its end.

The impedance of this line becomes $$Z_0 = \sqrt{\left(\frac{\mu_0 \epsilon_0}{2 C^a (C^a + C^s)}\right)} \qquad \text{Eq. 23}$$

When $\varepsilon_{reff}$ is complex, then the line impedance is also complex.

$$Z_0 = \sqrt{\left(\frac{\mu_0 \epsilon_0}{2 C^a (C^a + C^s)}\right)} \qquad \text{Eq. 24}$$

Matching into the electrodes is possible with a careful design of the matching structure, such as can include using Eq. 24.

Finite Thickness Substrate with Ground Plane

When a ground plane is used with the two parallel electrode structure, the two electrodes become coupled microstrip lines and the analytic expressions can be used. The capacitance Cp between the two strips, and the individual strip capacitances Cg to the ground plane can be determined. The coupled lines have even and odd modes, but in the excitation model, one of the electrodes can be grounded, in which case odd-even modes are not excited.

$$C_g = 2 \epsilon_0 \left[\frac{\epsilon_r K(k_1)}{K'(k_1)} + \frac{K(k_2)}{K'(k_2)}\right] \qquad \text{Eq. 25}$$

$$C_p = \epsilon_0 \left[\frac{\epsilon_r K(k_3)}{K'(k_3)} + \frac{K(k_4)}{K'(k_4)}\right] - \epsilon_0 \left[\frac{\epsilon_r K(k_1)}{K'(k_1)} + \frac{K(k_2)}{K'(k_2)}\right] \qquad \text{Eq. 26}$$

$$k_1 = \tanh\left(\frac{\pi \omega}{4h}\right) \tanh\left(\frac{\pi(\omega + s)}{4h}\right) \qquad \text{Eq. 27}$$

$$k_2 = \tanh\left(\frac{\pi \omega}{4(h + \pi\omega)}\right) \tanh\left(\frac{\pi(\omega + s)}{4(h + \pi\omega)}\right) \qquad \text{Eq. 28}$$

$$k_3 = \tanh\left(\frac{\pi \omega}{4h}\right) \coth\left(\frac{\pi(\omega + s)}{4h}\right) \qquad \text{Eq. 29}$$

$$k_4 = \frac{\omega}{\omega + s} \qquad \text{Eq. 30}$$

When the substrate is air, it has a permitivitty of $\varepsilon_o$, then the above capacitance expressions become $C_{ga}$ and $C_{pa}$ with $\varepsilon_r$ omitted in Equations 25 and 26. Then the expressions for the total air substrate capacitance Ca=Cga+Cpa and the total capacitance with the dielectric substrate present is Cd=Cg+Cp. Then the effective relative permittivity becomes:

$$\epsilon_{reff} = \frac{C^d}{C^a} \qquad \text{Eq. 31}$$

The impedance of the line becomes:

$$Z_0 = \sqrt{\frac{\mu_0 \epsilon_0}{C^a C^d}} \qquad \text{Eq. 32}$$

When $\varepsilon_{reff}$ is complex, then the line impedance is also complex. Matching into the electrodes is possible with a careful design of the matching structure, such as can include using Eq. 32.

Figure 6:
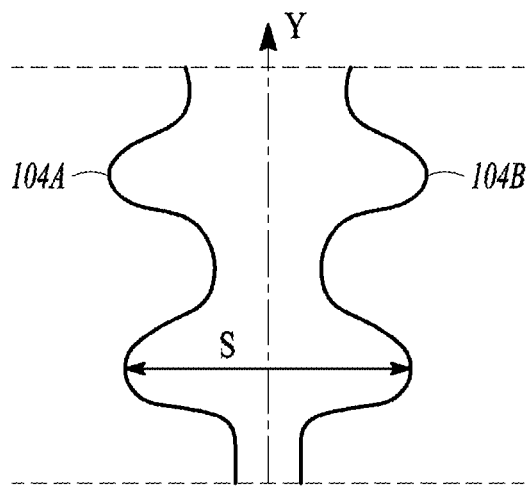
FIGS. 6-7 show examples of variation in electrode spacing, such as using serpentine or divergent electrodes.
Figure 7:
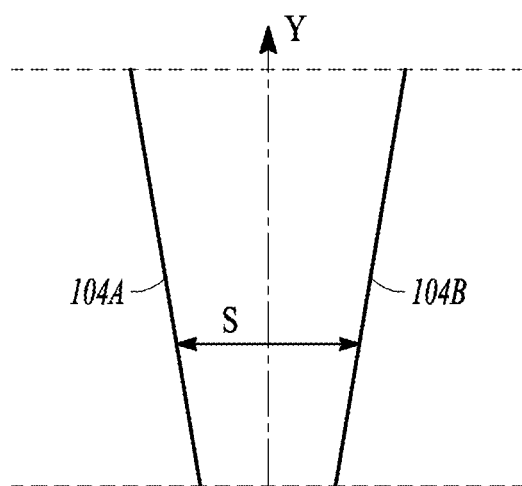

The equations explained above for the three example configurations can be used to relate spacing, inductance, and frequency for most configurations of the electrodes, such as for creating heat and, optionally, for establishing a temperature gradient. Such a temperature gradient can be established by varying the spacing between electrodes—at points on respective electrodes that are closer together, the substrate will become hotter than at points on respective electrodes that are farther apart. FIGS. 6-7 show examples of electrodes having variable electrode spacing, s, between nearest points on the respective electrodes. FIG. 6 shows an example of a serpentine electrode configuration. FIG. 7 shows an example of a diverging linear electrode configuration.

In general, for the configurations shown in FIGS. 6-7, the temperature in the y direction will be a function of frequency, F, and separation, s, such as expressed in the following equation.

$$T_y = F(F, s) \qquad \text{Eq. 33}$$

For each electrode geometry, one can calculate the maximum and minimum match frequencies corresponding to the maximum and minimum spacing. Each set of electrodes and substrate characteristics also has a triggering frequency for heat production. Frequencies below the triggering frequency do not produce heat, because there is insufficient energy transfer at such frequencies. An external impedance matching circuit can be added in series between the time-varying electric field signal generator circuit 108 and the capacitive electrodes 104A-B on the semiconductor substrate, such as to provide a desired impedance matching to permit heat production in the semiconductor substrate at a desired frequency.

As shown in Eq. 33, temperature at any pointy along the central axis is a function frequency (F) and spacing s. For any (frequency, spacing) combination, the temperature is maximum at location y where the match is complete or near complete. A gradient occurs on either side of y due to varying degrees of matching. By altering frequency one can effectively move the point of maximum heat generation, and by implication the gradient, up and down along the y axis. The flow chart shown in FIG. 3 describes an example of a process that can be used to control such a device, such as to establish a desired temperature gradient. The case of parallel electrodes is a special case in which spacing between the electrodes is constant, and thus the percentage of matching is the same along the entire electrode length, which does not permit a temperature gradient in this fashion in the absence of losses occurring along the length of the electrodes in the y-direction.

However, one can also create a temperature gradient by placing heat sinks or cooling cells at different locations on the substrate. Each cooling cell can be controlled separately or independently, such as by the control circuit 107 or by an external microprocessor based control system that can manage the heat output of each cell to establish and manage a temperature gradient.

For a heat production application with sufficient space and sufficiently coarse control, the length of the electrode can be adjusted such that all of the energy from the time-varying signal provided by the electric field signal generator 108 can be dissipated along the length of the electrode. A temperature gradient can be formed because the amount of energy transferred or left in the signal decreases as the signal traverses the length of the electrode. Further control on heat production can be exercised by adjusting the amplitude of the input signal, such as in cases in which a maximum frequency has been reached, as explained in FIG. 3.

Example of Experimental Results

Preliminary laboratory experiments were conducted to test the viability of the present approach to time-varying frequency-controlled heat production in a semiconductor substrate.

A p-type <100> silicon semiconductor wafer substrate with resistivity in the 15-25 ohms/cm$^2$ range was used. A 1000 Angstrom layer of silicon dioxide (SiO2) was grown on a top surface of the silicon wafer. Two parallel 1.5 centimeter long strips of copper metallization were formed upon the SiO2 on the silicon wafer as electrodes. The spacing between electrodes was 1.5 millimeters in this specimen.

A Signatone probe station was used. The specimen was placed on an insulated jig on the copper base plate of the probe station, to inhibit or prevent the base plate from acting as a heat sink. A frequency generator with a range of up to 900 MHz was provided for connection to the electrodes in a quiet semi-dark room with a temperature controlled environment that was maintained at room temperature of 26 degrees Celsius. Any focused lamps were turned off after being used for establishing probe contacts with the specimen. For injecting the time-varying frequency signal onto the electrodes, an RF GGB Pico probe was used (GS configuration) to inhibit RF spatter. A 1 Watt amplifier was placed in series with the input signal probe. An RTD temperature sensor was used for measuring the semiconductor substrate temperature and another was left to monitor a reference room temperature measurement. Table 1, below, shows the experimental results of the change of the temperature of the semiconductor substrate (for a single sample of the semiconductor substrate) as a function of change of frequency of the input signal. The duration between changes in input frequency was set to 5 minutes to help provide steady-state data for each frequency.

TABLE 1

| | Substrate Temperature vs. Frequency | |
|---|---|---|
| Frequency (MHz) | Temp (C.) reading cycle 1 | Temp (C.) reading cycle 2 |
| 80 | No change | No change |
| 180 | No change | No change |
| 300 | No change ( some change was seen but unable to stabilize thus was deemed inconclusive) | No change |
| 500 | 32.8 | 32.8 |
| 700 | 34 | 33.6 |
| 900 | 36.8 | 37.4 |

As a further verification that frequency was the only change to the overall all experimental setup affecting the temperature changes we randomly changed frequency up and down to the values shown in the table. Each time the temperature stabilized at the same value for the particular frequency.

In this document, the term "substrate" includes the active material layer that actively produces heat by the capacitively coupled non-zero frequency time-varying electric field applied thereto. Other types of material layers may be attached to the active layer or layers, such as for heat extraction or for one or more other application specific needs. The substrate can include a single type of semiconductor material or a composite material, which can include multiple types of semiconductor materials, one or more Peltier materials, or one or more other application-specific materials. A composite can be created, for example, by bonding one or more types of materials though one or more bonding processes such as, e.g., direct bonding, glue or adhesive, etc. In an example, a thin film metal material and a semiconductor material can be bonded together, and either or both can function as the active heat source, such as concurrently.

Ohmic contacts can be used to operate under similar principles as described herein for capacitive coupling, except without capacitive coupling the displacement current does not occur. Still, localized control of heat generation, such as by controlling the frequency of the applied electrical signal, is believed to be possible using ohmic contacts as well as using capacitive contacts. FIGS. 8A-8 shows several substrate examples. In FIG. 8A, capacitive electrodes 804A-B can be located upon a semiconductor, thin-film metal, or other substrate 802, e.g., separated therefrom by an electrical insulator or dielectric layer 803A-B.

In FIG. 8B, the electrical insulator 803A-B can be omitted and the electrodes 804A-B can be located on the substrate 802, such as Schottky diode contacts, which can include a semiconductor or thin-film metal substrate forming a Schottky diode connection with the electrodes 804A-B.

In FIG. 8C, the substrate can include a composite substrate 802, such as can include multiple substrates 802A-B that can be bonded together to provide a combination of one or more substrate characteristics (e.g., lattice alignment, doping type or concentration or both, etc.) that are suitable for a particular application. For example, a semiconductor or thin-film metal substrate 802A, which can be bonded to a Peltier material substrate 802B, such as by an electrical insulator 803A-B. The electrical insulator 803A-B can be thermally conductive, e.g., using a bonding material having a specified thermal conductivity, which can be specified to be higher than the thermal conductivity of one or both of the substrates 802A-B. In an example, the Peltier material can include bismuth telluride.

In an example, one or both of the substrates 802A-B can be actively excited through a capacitively coupled non-zero frequency time-varying electric field, such as by a set of capacitive electrodes that can be shared between the substrates 802A-B (e.g., sandwiched between the substrates 802A-B) or separately dedicated to a respective individual substrate 802A (e.g., located upon faces of the substrates 802A-B that are opposite from an adjacent face between the substrates 802A-B).

FIG. 8D shows an example in which multiple electrodes 804A-B can be sandwiched between the substrates 802A-B without an electrical insulator intervening between the electrodes 804A-B and the respective substrates 802A-B, such as in an arrangement in which Schottky capacitive contacts are desired.

FIG. 8E shows an example in which multiple electrodes 804A-B can be sandwiched between the substrates 802A-B with a respective electrical insulator 803A-D intervening between the electrodes 804A-B and the respective substrates 802A-B, such as in an arrangement in which non-Schottky capacitive contacts are desired.

FIG. 8F shows an example in which electrodes 804A-B are separated from a thin-film metal substrate 802A by an insulator 803A-B, such as with the thin-film metal substrate 802A being deposited or otherwise formed upon an underlying supporting substrate 802B, which, in an example, can include a heat sink material having greater thermal conductivity than the thin-film metal substrate 802A and lower electrical conductivity than the thin-film metal substrate 802A. In an example, the heat sink material of the supporting substrate 802A can include diamond or an intrinsic or lightly-doped semiconductor material.

VARIOUS NOTES

The above description includes references to the accompanying drawings, which form a part of the detailed description. The drawings show, by way of illustration, specific embodiments in which the invention can be practiced. These embodiments are also referred to herein as "aspects" or "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus comprising:
an article of manufacture, comprising an active heat source including:
a substrate; and
electrodes, formed at manufacture to be located directly or indirectly on the substrate, the electrodes configured to receive a non-zero frequency time-varying electrical energy that is coupled by the electrodes to the substrate to generate a particular frequency-controlled heating region in the substrate, the particular heating region location frequency-selectable preferentially from among different locations along a length of the electrodes in accordance with the frequency of the time-varying electrical energy.

2. The apparatus of claim 1, wherein the heating region location is moved along a length of the electrodes by adjusting the frequency of the time-varying electrical energy.

3. The apparatus of claim 1, wherein the electrodes include first and second electrodes separated from each other by different minimum spacing at different locations one the electrodes.

4. The apparatus of claim 1, wherein the substrate includes a semiconductor substrate.

5. The apparatus of claim 1, wherein the substrate includes a material having an effective relative permittivity that is complex-valued such that it includes an imaginary component.

6. The apparatus of claim 1, wherein the electrodes are capacitively coupled to the substrate.

7. The apparatus of claim 1, comprising a temperature sensor, located in association with the substrate to sense a temperature associated with the substrate.

8. The apparatus of claim 1, wherein the electrodes include first and second electrodes separated by a spacing that is specified to be less than or equal to a spacing value capable of generating heat in the substrate, without requiring net charge flow into or out of the substrate via pass-through conduction current, in response to the time-varying electrical energy received at the electrodes.

9. The apparatus of claim 1, wherein the electrodes include electrically conductive material that is adjacent to a dielectric material.

10. The apparatus of claim 1, wherein the temperature of the substrate is adjusted by direct heating of the substrate by an electromagnetic field in the substrate produced by the time-varying electrical energy applied to the electrodes.

11. The apparatus of claim 1, wherein the electrodes include a first electrode comprising a first trace and a second electrode comprising a second trace that is separated from the first trace by a specified distance.

12. The apparatus of claim 11, wherein the specified distance is constant along a length of the first and second traces.

13. The apparatus of claim 11, wherein the specified distance is mirrored along a central axis defined between the first and second traces.

14. The apparatus of claim 11, wherein the specified distance diverges or otherwise varies along a central axis defined between the first and second traces.

15. The apparatus of claim 1, wherein at least one of the electrodes includes at least one of a ground plane or a electrical return path.

16. The apparatus of claim 1, wherein the electrodes are configured to receive a non-zero frequency time-varying electrical energy that is coupled by the electrodes to the substrate to generate a frequency-controlled oscillation of charged particles within the substrate.

17. A method of establishing or adjusting a temperature of a heating element, the method comprising:
obtaining or providing an article of manufacture comprising an active heating region including a substrate and electrodes;
receiving, via the electrodes, non-zero frequency time-varying electrical energy that is electromagnetically coupled by the electrodes to the substrate to generate a frequency-controlled heating region in the substrate;
tuning a frequency of the time-varying electrical energy to specify a particular location of heat in the substrate along a length of the electrodes, the particular location frequency-selectable preferentially from among different locations along a length of the electrodes in accordance with the frequency of the time-varying energy; and
establishing or adjusting a temperature of the substrate, including controlling the particular location by controlling the frequency of the electrical energy received at the electrodes.

18. The method of claim 17, comprising tuning a frequency of the time-varying electrical energy to move a location of heat in the substrate along a length of the electrodes.

19. The method of claim 17, comprising capacitively coupling the time-varying electrical energy from the electrodes to the substrate.

20. The method of claim 17, comprising:
sensing a temperature associated with the substrate;
using information about the sensed temperature, establishing or adjusting at least one of (1) an amplitude of the time-varying electrical energy generated by the electric field signal generator; (2) a frequency of the time-varying electrical energy generated by the electric field generator; or (3) a location or distribution of a current path between at least two of the electrodes.

21. The method of claim 17, comprising electromagnetically coupling the non-zero frequency time-varying electrical energy from the electrodes to the substrate to generate a frequency-controlled heating region in the substrate without requiring net charge flow into or out of the substrate via pass-through conduction current.

22. The method of claim 17, wherein the establishing or adjusting a temperature of the substrate, includes direct heating of the substrate by an electromagnetic field produced by the time-varying electrical energy, without requiring indirect heat coupling to the substrate.

23. The method of claim 17, wherein the establishing or adjusting a temperature of the substrate includes controlling the frequency of the electrical energy received via at least one of the electrodes to establish or adjust a temperature gradient of the substrate.

24. The method of claim 17, comprising electromagnetically coupling the non-zero frequency time-varying electrical energy from the electrodes to the substrate to generate a frequency-controlled oscillation of charged particles within the substrate.

25. An apparatus comprising:
an article of manufacture, comprising an active heating region including:
a substrate; and
electrodes, formed at manufacture to be located directly or indirectly on the substrate, the electrodes configured to receive a non-zero frequency time-varying electrical energy that is coupled by the electrodes to the substrate to generate a particular frequency-controlled heating region in the substrate, the particular heating region location moved along a length of the electrodes by adjusting the frequency of the time-varying electrical energy to frequency-select the particular heating location preferentially from among different locations along a length of the electrodes in accordance with the frequency of the time-varying electrical energy.

* * * * *